United States Patent [19]

Driggers et al.

[11] Patent Number: 4,814,702

[45] Date of Patent: Mar. 21, 1989

[54] PROCESS FOR ACCURATELY DETERMINING THE POSITION OF THE EDGES OF SUPPORT PLATES IN STEAM GENERATORS

[75] Inventors: John M. Driggers, Pittsburgh; James C. J. Yeh, Murrysville, both of Pa.

[73] Assignee: Westinghouse Electric Corp., Pittsburgh, Pa.

[21] Appl. No.: 615,868

[22] Filed: May 31, 1984

[51] Int. Cl.[4] .......................... G01B 7/14; G01B 7/24
[52] U.S. Cl. ................................ 324/207; 324/220; 324/236; 324/225
[58] Field of Search .................... 324/219–222, 324/225–243, 262; 165/11.2; 336/232, 220, 180, 183, 207, 208

[56] References Cited

U.S. PATENT DOCUMENTS

| | | | |
|---|---|---|---|
| 2,540,588 | 2/1951 | Long | 324/219 X |
| 3,302,105 | 1/1967 | Libby et al. | 324/233 |
| 3,434,046 | 3/1969 | Wilson et al. | 324/221 |
| 3,845,381 | 10/1974 | Hart | 324/221 |
| 3,890,564 | 6/1975 | Watanabe et al. | 324/233 X |
| 3,916,301 | 10/1975 | Vild et al. | 324/226 |
| 4,017,704 | 4/1977 | Collins, III et al. | 336/232 X |
| 4,072,894 | 2/1978 | Barton | 324/221 |
| 4,172,492 | 10/1979 | Abell et al. | 165/11.2 |
| 4,182,985 | 1/1980 | De Wolfe et al. | 324/220 |
| 4,194,149 | 3/1980 | Holt et al. | 324/220 |
| 4,287,655 | 9/1981 | Gerkey et al. | 29/407 |
| 4,325,026 | 4/1982 | Cooper, Jr. et al. | 324/232 |
| 4,341,113 | 7/1982 | Gutzwiller, Jr. | 324/200 X |
| 4,412,177 | 10/1983 | Petrini et al. | 324/226 |
| 4,425,296 | 1/1984 | Adamowski et al. | 376/245 |
| 4,441,078 | 4/1984 | Lecomte | 324/219 |
| 4,480,225 | 10/1984 | Hance et al. | 324/220 X |

FOREIGN PATENT DOCUMENTS

| | | | |
|---|---|---|---|
| 2837488 | 12/1979 | Fed. Rep. of Germany | 324/219 |
| 2937865 | 4/1981 | Fed. Rep. of Germany | 324/222 |
| 0119845 | 9/1981 | Japan | 324/232 |

*Primary Examiner*—Reinhard J. Eisenzopf
*Assistant Examiner*—Warren S. Edmonds

[57] ABSTRACT

A process for using an eddy current probe to precisely locate the edges of a baffle plate or support plate which surrounds a tube of a heat exchanger is disclosed herein. The process generally comprises the steps of moving the eddy current probe through the interior of the tube in the vicinity of the plate with the axis of rotation of the coil oriented parallel to the longitudinal axis of the tube. The rate of change of coil impedance is monitored as a function of the position of the coil along the longitudinal axis of the tube. When the rate of change of current flow through the coil attains its first maximum, the mid-plane of the coil is parallel to the bottom edge of the plate. This process is particularly useful in implementing maintenance procedures wherein heat exchanger tubes are selectively expanded along certain portions of their longitudinal axes in order to eliminate or reduce unwanted clearance between the tubes and the bores in the support plates through which they extend. The process may also be used to confirm whether or not a tube expansion has been performed in proper position in a tube relative to a particular support plate.

28 Claims, 4 Drawing Sheets

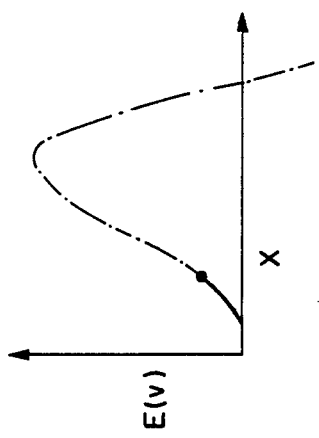
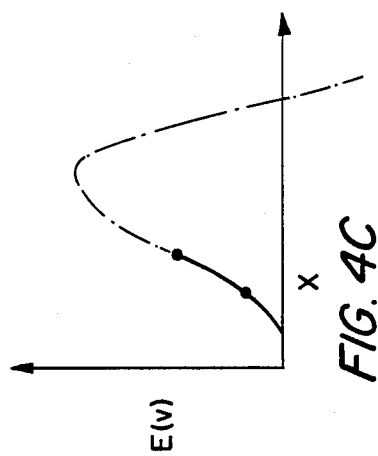
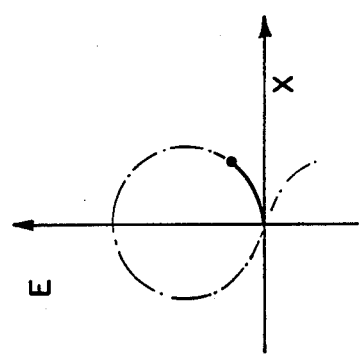
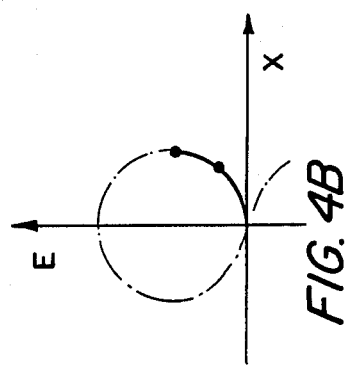
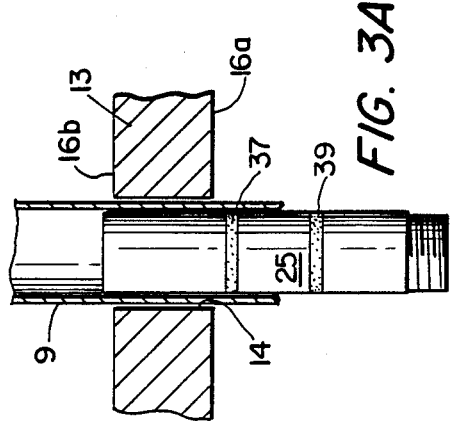
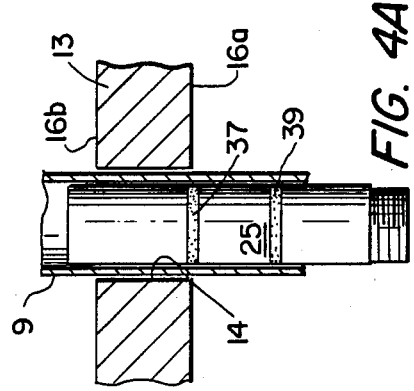

PROCESS FOR ACCURATELY DETERMINING THE POSITION OF THE EDGES OF SUPPORT PLATES IN STEAM GENERATORS

BACKGROUND OF THE INVENTION

1. Field of the Invention

This invention relates to a process for using an eddy current probe to accurately determine the location of the top and bottom edges of plates used to uniformly space the heat exchange tubes in a nuclear steam generator.

2. Description of the Prior Art

Processes for using eddy current probes to locate the positions of baffle plates and support plates in nuclear steam generators are known in the prior art. An example of the use of such a probe is disclosed in U.S. patent application Ser. No. 567,107, filed Dec. 30, 1983, and assigned to Westinghouse Electric Corporation, the entire specification of which is hereby expressly incorporated herein by reference. Such eddy current probes are particularly useful in implementing maintenance procedures in nuclear stem generators which require the radial expansion of selected portions of heat exchanger tubes. To fully appreciate the role played by such probes in these procedures, some background in the maintenance problems and procedures associated with such steam generators is necessary.

Nuclear steam generators generally include a primary side through which hot, radioactive water from the reactor core is admitted into a plurality of heat-exchange tubes which may be either U-shaped or straight. Such generators further include a secondary side which houses and spaces these tubes and circulates a flow of non-radioactive water therethrough so that non-radioactive steam may be generated from the energy output of the reactor core. The tubes of the steam generator transfer heat from the radioactive water flowing through their inside surfaces to the non-radioactive water flowing over their outside surfaces. To facilitate this heat transfer, a plurality of horizontally disposed baffle plates and support plates are mounted throughout the secondary side of the steam generator in order to uniformly space the heat-exchanging tubes from one another. Each of these plates includes a plurality of uniformly-spaced openings (which may be bores) through which the tubes extend. The openings of the plates are arranged in registry with one another in order that the heat-exchange tubes may be arranged parallel to one another. In order to increase thermal contact between the outside surfaces of the heat-exchange tubes and the non-radioactive water flowing through the secondary side inlet, the baffle plates of the generator are placed in a staggered arrangement to cause the water circulating through the secondary side of the generator to weave back and forth in a serpentine pattern. Unfortunately, the fluid currents associated with such a tortorous flow of water sometimes causes these tubes to vibrate against the walls of the bores in both the baffle plates and the support plates. The resultant mechanical shock can dent the tubes, and cause wear scars by disrupting the crystalline structure of the Inconel which typically forms these tubes. These dents and wear scars render the outside surfaces of the tubes subject to corrosion degradation from the salts and sludges which are present in the non-radioactive water which flows through the secondary side of the generator. Ultimately, the vibration caused by the heat exchange tubes rattling against the sides of the bores in the baffle plates and support plates may cause a significant number of these tubes to corrode until they crack, and radioactively contaminate the water flowing through the secondary side of the steam generator.

In order to solve the problems associated with such destructive tube vibration, maintenance procedures have been developed wherein the mandrel of a hydraulic expansion unit is inserted up through the vibrating tube in order to radially expand the tube in the vicinity of the bores of the baffle plates and support plates. This radial expansion in the tube reduces or eliminates the gap between the outer walls of the tube and the walls of the bore or other opening in the plate through which it extends, thereby preventing the opportunity for the tube to rattle against the walls of the bores. However, the successful implementation of such tube expansions relies in part on the proper axial alignment of the hydraulic expansion mandrel with the region of the tube surrounded by the bore of the plate. If the center of the expansion mandrel is not closely aligned with the center line of the plate surrounding the tube, part of the radially expanded walls of the tubes may bulge over either the top or bottom of the plate, thereby creating a substantial amount of strain in the crystalline structure of the Inconel forming the heat exchange tubes. Experience has shown that the strained areas of such tubes are more susceptible to the corrosion degradation which can lead to cracking.

In order to properly align the hydraulic expansion mandrels within such tubes so that the tubes are radially expanded without such destructive bulging, the prior art has employed eddy current probes utilizing a pair of axially aligned sensing coils. When these coils are connected to commercially available eddy current circuitry, wherein the current differential between the two coils is accurately monitored by means of an oscilloscope connected across an impedance-type bridge, a null-point signal will be generated when the coils are symmetrically diposed about the center line of the plate. Unfortunately, the accuracy of this null-point signal is dependent upon the existence of complete geometric symmetry in the bore through the plate. Inaccuracies may arise if one of the edges of the bores is chamfered or bevelled while the other edge is not. Additionally, such a null-point signal is capable of positively indicating the position of only one of the plate edges (assuming that the coils are spaced apart the same distance as the thickness of the plate).

Hence, there is a need for a process wherein an eddy current probe can more accurately detect the position of both the edges of a plate in a steam generator in order that a hydraulic expansion mandrel may be properly positioned incident to a tube expansion. Moreover, in view of the potentially destructive effects associated with tube bulging, there is a need for a process wherein an eddy current probe accurately and conveniently detects when a tube expansion has resulted in a bulge condition so that potential corrosion problems associated with the bulge may be prevented either by sleeving or plugging operations.

SUMMARY OF THE INVENTION

In its broadest sense, the invention is a process of using an eddy current probe to accurately locate the edges of a structure by noting the rate of change of the impedance of the probe coil as the probe is moved adjacent the structure. In steam generators where a plurality of heat exchange tubes extend through one or more support plates, the process of the invention is well suited for accurately locating the top and bottom edges of these plates with respect to the longitudinal axes of the heat exchange tubes. As indicated earlier, such information is highly useful both for implementing a tube expansion in order to reduce the clearance between the tube and the support plate, as well as for evaluating the success of the hydraulic tube expander in accurately confining the expansion to only that area surrounded by the support plate.

The process of the invention generally comprises the steps of moving an eddy current probe through the tube through the vicinity of the plate or other structure, while monitoring the rate of change of current flow through the coil as a function of the position of the coil along the longitudinal axis of the tube. The position of the coil along the longitudinal axis of the tube is noted when the rate of change of impedance through the coil attains its first maximum. The applicants have empirically found that this first maximum occurs when the mid-plane of the coil is parallel to the bottom edge of the support plate.

The process may further include the step of noting when the second maximum rate of change of impedance occurs in the coil as it is moved through the vicinity of the tube surrounded by the plate in order to ascertain the location of the top edge of the support plate.

The process may further include the use of an eddy current probe which includes two substantially identical coils having coincident axes of rotation. If such a probe is used, substantially identical A.C. currents are passed through each of the coils, and the differential current flow is monitored as a function of the longitudinal position of one of the coils in the conduit or tube. The position of the monitored coil along the longitudinal axis of the conduit or tube is noted when the rate of change of the differential current flow attains its first maximum, which again indicates that the mid-plane of the leading coil is parallel with one of the edges of the plate or other structure surrounding the conduit or tube. This embodiment of the process of the invention may also include the additional step of noting the position of the leading coil along the longitudinal axis of the conduit or tube when the null point (indicative of a zero amount of differential current) occurs. The null point indicates that the leading and trailing coils are equidistantly spaced about the center line of the plate. Finally, the process may include the step of noting when the second maximum in the rate of change of the differential current occurs. This second maximum indicates that the plane of the trailing coil is now parallel with the other edge of the baffle plate or other structure surrounding the conduit or tube.

A second embodiment of the process of the invention is particularly well adapted toward determining whether or not the longitudinal limits of a tube expansion extend beyond the length of the support plate suurrounding the tube. In this embodiment, a higher frequency current is passed through one of the coils (preferably the leading coil) while a lower frequency coil is passed through both coils. The leading and trailing coils are next moved through the tube through the vicinity of both the tube expansion and the surrounding plate. The change of the impedance of the leading coil to the higher frequency current flow is monitored. At the same time, the rate of change of the differential current flow between the lower frequency current flows in both the leading and trailing coils is monitored. The length and position of the tube expansion are ascertained by noting the position of the dual frequency leading coil along the longitudinal axis of the tube when substantial changes occur in the impedance of said higher frequency current through the leading coil. Next, the length and position of the structure across the longitudinal axis of the tube are ascertained by noting the position of the dual frequency leading coil when the rate of change of the differential current flow of the second frequency attains a first maximum and then a null point. Finally, the longitudinal limits and position of the tube expansion are compared with the longitudinal limits and position of the edges of the support plate to ascertain whether or not the expansion is properly located within the opening in the support plate.

BRIEF DESCRIPTION OF THE SEVERAL FIGURES

FIG. 3A illustrates the probe of FIG. 2A, approaching the bottom edge of a support plate surrounding a heat exchange tube;

FIGS. 3B and 3C illustrate the increase in the differential current between the leading and the trailing coils of the eddy current probe as it approaches the support plate, both with reference to the oscilloscope presentation and the vertical component of the composite waveform of the differential current, respectively;

FIG. 4A illustrates the eddy current probe of FIG. 2A with the plane of its leading coil parallel to the bottom edge of a support plate;

FIGS. 4B and 4C illustrate how the differential current flow between the leading and the trailing coils attains a maximum when the eddy current probe is in the position illustrated in FIG. 4A, both with respect to the oscilloscope presentation and the inflection point in the vertical component of the composite waveform, respectively;

Figure 7A:
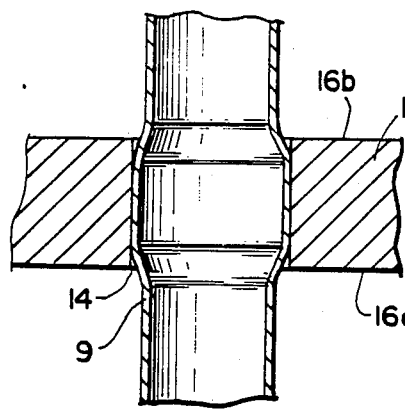
FIG. 7A illustrates a properly-formed tube expansion within the bore of a surrounding support plate.
Figure 7B:
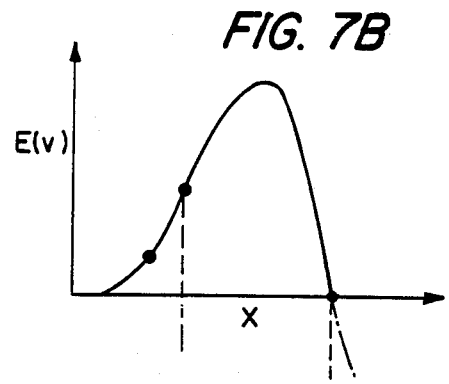
Figure 7C:
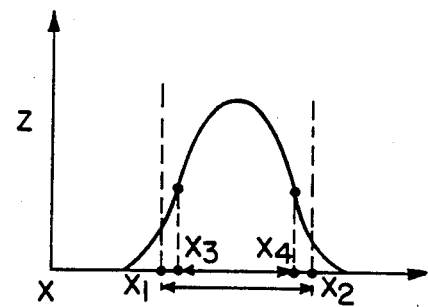

FIG. 7B indicates the location of the edges of the support plate of FIG. 7A along the longitudinal axis of the tube by means of the vertical component of the composite waveform of the differential current lowing between the leading and trailing coils of the eddy current probe, and FIG. 7C illustrates the location of the expansion in the tube of FIG. 7A relative to the edges of the support plate by means of the impedance curve Z generated by the leading coil of the eddy current probe when operated in the absolute mode.

DETAILED DESCRIPTION OF THE PREFERRED EMBODIMENT

Overview of the Purpose and Implementation of the Process of the Invention

Figure 1:
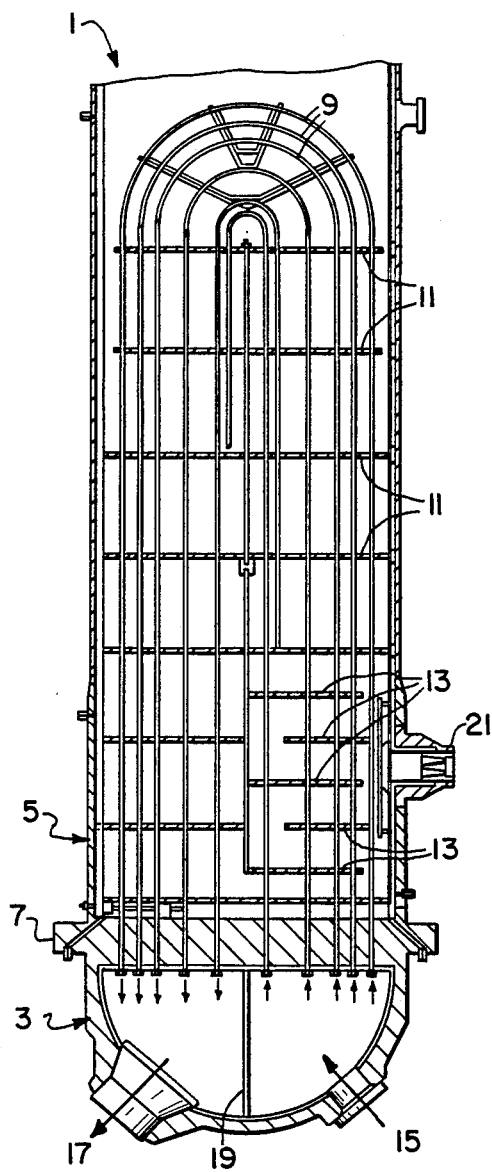
FIG. 1 is a cross-sectional view of a nuclear stem generator, illustrating both the heat exchange tubes used in such generators, as well as the support and baffle plates which uniformly space these tubes from one another.

With reference now to FIG. 1, wherein like numerals designate like components throughout the several figures, the process of the invention is particularly adapted for effecting expansions of selected sections of the tubes 9, which may be U-shaped as shown, in a nuclear steam generator 1. Before the utility of such tube expansions can be appreciated, some understanding of the general structure and maintenance problems associated with such steam generators 1 is necessary.

Nuclear steam generators 1 generally include a primary side 3 and a secondary side 5 which houses a plurality of U-shaped heat exchange tubes 9. The primary side 3 is divided into two compartments by a divider plate 19. Hot, radioactive water from the reactor core flows into the right-hand section of the primary side 3 and enters the inlets of the U-shaped tubes 9 as indicated. From this point, the hot, radioactive water flows completely around the U-shaped tubes 9 in the secondary side 5 of the generator 1, and out into the left-hand portion of the primary side 3, and out of the outlet 17 as indicated. While hot water is flowing through the interiors of the U-shaped tubes 9, non-radioactive water from secondary side inlet 21 flows over the outside surfaces of these tubes. The tubes transfer heat from the radioactive water to the non-radioactive water. In order to maximize the amount of heat transfer between the tubes 9 and the non-radioactive water flowing over them from inlet 21, a plurality of support plates 11 and baffle plates 13 are provided in the body of the generator 1 in order to uniformly space the legs of the U-shaped tubes 9 in uniform, parallel alignment with one another. To this end, each of the plates 11 and 13 include a plurality of bores 14 which are in mutual registry with one another so that the tubes 9 are arrayed in a parallel and uniformly spaced relationship when the legs of these tubes 9 are inserted through these bores 14.

As previously indicated, the fluid currents generated by the water flowing through the secondary side 5 of the generator 1 can cause the legs of the U-shaped tubes 9 to vibrate against the walls of the bores 14 or other openings in the support plates 11 and baffle plates 13. The mechanical shock produced by such vibration can render the walls of the tubes 9 more prone to corrosion degradation, which can seriously weaken the walls of the tubes 9. To prevent such corrosion degradation and the consequent weakening of the walls of the tubes 9, the process of the invention may be used to accurately locate the edges of the support plates 11 and the baffle plates 13 so that the walls of these tubes 9 might be precisely expanded by means of a hydraulic expansion mandrel to eliminate or at least reduce the clearance between the tubes 9 and the bores 14 in the plates 11 and 13. As may presently be seen, the process of the invention may also be used to determine whether or not such a tube expansion is accurately positioned between the top and bottom edges of the plates 11 and 13. This second application of the process of the invention provides a convenient and accurate way in which to determine whether or not a bulge which is outside of the plate edges has been created in the walls of the tube 9 through either an improper positioning of the hydraulic expansion mandrel, or the application of too much pressure on the inner walls of the tube 9. Such a bulge generates a strain condition in the tube which dislocates the crystalline structure of the Inconel forming the walls of the tubes 9, which in turn renders the tubes substantially more prone to corrosion degradation.

Figure 2A:
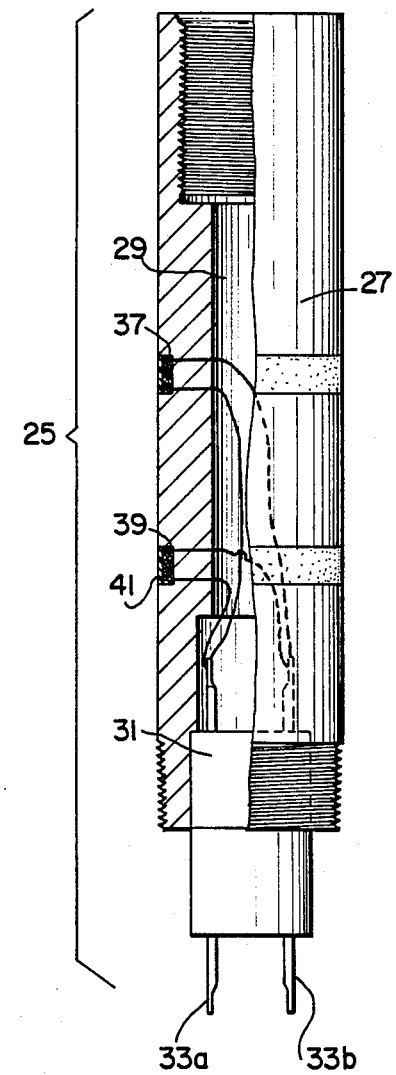
FIG. 2A is a partial cross-sectional view of the preferred embodiment of the eddy current probe used in the process of the invention.

FIG. 2A illustrates the preferred embodiment of the eddy current probe 25 used to implement the process of the invention. The eddy current probe 25 includes a generally cylindrical probe body 27 which is preferably formed from either nylon or machined Delrin ®. Probe body 27 includes a hollow and substantially cylindrical interior 29 which houses an electric socket 31 at its lower end. The upper end of the probe body 27 includes a set of threads which may accommodate either a top end cap or the end-fitting of the inventive hydraulic expansion mandrel disclosed in the aforementioned U.S. patent application Ser. No. 567,107. The bottom end of the probe body 27 likewise includes a set of threads which may accommodate a coupling assembly between this end of the probe body 27, and a coaxial cable leading to the eddy current circuitry.

Eddy current probe 25 includes first and second sensing coils 37 and 39 as shown. While the axes of the coils 37 and 39 are preferably coextensive, applicants believe that the process of the invention can also be implemented without such coextensiveness, although at the cost of some of the high degree of accuracy of which this invention is capable with respect to locating plate edges. With respect to the coil terminology used throughout this specification, ether coil may function as the "leading" coil or the "trailing" coil, depending on which coil is first inserted through the portion of the tube 9 surrounded by the bore 14 of the plate 13 during the monitoring of the differential current between the two coils 37 and 39. Henceforth, it shall be assumed that the probe 25 is inserted up through the bottom edge of the plate 13, and that coil 37 acts as the leading coil. However, coil 39 could just as easily function as the leading coil if the probe were inserted entirely through the portion of the tube 9 surrounded by the bore 14 and then pulled back through the tube 9.

Turning now to the specific structure of the coils 37 and 39, each includes about 200 windings, and has a resistance of approximately 12 ohms. Applicants believe that the invention is best implemented if the leading coil 37 and the trailing coil 39 are both flat, bobbin-shaped coils having a length substantially smaller than their respective radii. For example, when the diameter of the probe body 27 is 1.60 cm. thick, each of the coils 37 and 39 includes a length preferably equal to or less than 0.15875 cm. Such a relatively flat coil shape concentrates the magnetic field lines generated by the coils 37 and 39 along the circular plane of each coil, which in turn allows a sharp resolution of the bottom and top edges of the plates 11 and 13 during the process of the invention.

Furthermore, the impedance and inductance is preferably the same between the two coils, within an error of ±1% or less. Preferably, the radial edge of each of the coils 37 and 39 falls a short distance below the outside surface of the probe body 27. This small gap left between the radial edges of the coils 37 and 39 and the cylindrical outer surface of the probe body 27 is filled with an epoxy resin in order to protect the delicate windings of the coils, and to render the surface of the probe body flush at all points. Finally, terminals 33a and 33b of the electric socket 31 are connected to the input and output, respectively, of the leading coil 37, while terminals 35a and 35b (not shown) of the electric socket 31 are connected to the input and output, respectively, of the trailing coil 39.

Figure 2B:
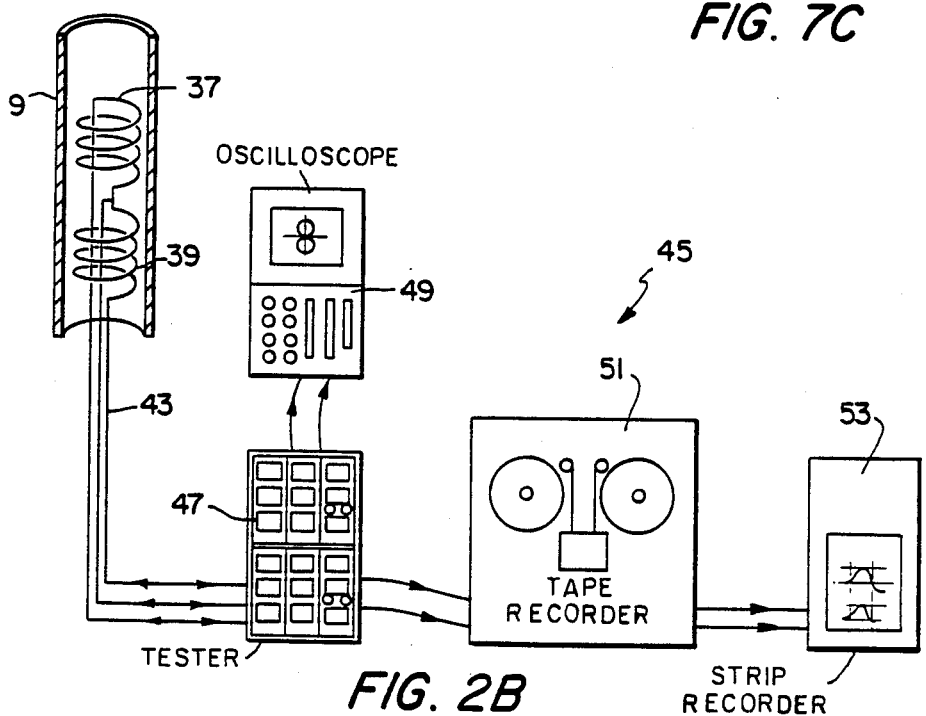
FIG. 2B is a generalized schematic diagram of the circuitry used in connection with the eddy current probe of FIG. 2A.

With reference now to FIG. 2B, the preferred eddy current circuitry 45 used is a MIZ-12 frequency multiplexer, manufactured by Zetec, Inc. of Isaquah, Wash. This eddy current circuitry includes a tester 47 capable of conducting A.C. currents of different frequencies to the input leads of either or both of the coils 37 and 39, and of conducting the output currents of these coils across an inductive bridge or other calibrated circuitry. The output of the inductive bridge of the tester 47 is connected both to an oscilloscope 49, as well as to a 2-channel strip recorder 53 via tape recorder 51 as indicated. The terminals 33a, 33b and 35a, 35b (not shown) of the electric socket 31 are connected via coaxial cable 43 to the Zetec unit so that the leading coil 37 may be used simultaneously in the "absolute" mode, as well as the "differential" mode, in conjunction with the trailing coil 39. While Zetec-type units are preferred, it should be noted that any eddy current probe circuitry capable of generating single or multiple frequency currents may be used to implement the process of the invention.

DETAILED DESCRIPTION OF THE PREFERRED EMBODIMENTS OF THE INVENTION

One preferred embodiment of the process of the invention is particularly well suited for accurately determining the position of the edges of a baffle plate 13 in preparation for a tube expansion. This particular embodiment of the invention is illustrated in FIGS. 3A, 3B and 3C, through FIGS. 6A, 6B and 6C.

With specific reference now to FIG. 3A, the previously described probe 25 is slid up through the heat exchange tube 9 to be expanded with both its leading coil 37 and its trailing coil 39 connected to the previously described eddy current probe circuitry 45 so that alternating currents of identical voltage, frequency and phase may be conducted through these coils. While the plane of the generally flat coils 37 and 39 is preferably oriented parallel to the bottom and top surfaces 16a and 16b of the plate 13 when the probe 25 is slid up through the tube 9, the process of the invention could be implemented with a non-parallel alignment between the plane of the coils 37, 39 and the surfaces 16a, 16b. In order to maximize the amount of electromagnetic coupling between the metal in the baffle plate 13 and the coils 37 and 39, the eddy current circuitry is adjusted so that a relatively low frequency alternating current is simultaneously passed through both of the coils 37 and 39. Such a relatively low frequency current allows the magnetic fields generated by the coils 37 and 39 to penetrate through the walls of the Inconel tube 9 and generate eddy currents in the plate 13 as the radial plane of at least one of these coils approaches the proximal edge of the plate 13 defined by the lower surface 16a of the plate, and the wall of the cylindrical bore 14. Applicants have found in practice that a frequency of 10 kHz is effective for the purpose of the invention, although other frequencies could also be used.

When leading coil 37 is in approximately the position illustrated in FIG. 3A, the fluctuating magnetic field generated by the alternating current flowing through this coil begins to generate eddy currents in the metallic plate 13. The generation of such eddy currents begins to change the impedance of the leading coil 37, which in turn reduces the net amount of current which flows through this coil, and may change the phase angle between the sinusoidal voltage curve and the current curve of this current. As previously mentioned, the output currents of the two coils 37, 39 are connected on either end of an electrical bridge inside the eddy current circuitry 45. Whenever there is an imbalance in the impedances between either of these coils, a differential alternating current will flow through the bridge which may be displayed in terms of a voltage and phase change curve on an oscilloscope, as shown in FIG. 3B.

The voltage and phase change curve of FIG. 3B is a lissajous figurine which includes both a vertical voltage component and a horizontal voltage component, each of which is separately traceable by means of the two-channel chart recorder 53. As the vertical voltage component of the voltage and phase change curve of FIG. 3B has been shown in practice to be the more informative of the two voltage components, the process of the invention shall be described in terms of this vertical voltage component, rather than the horizontal voltage component. FIG. 3C illustrates this vertical component E(v) of voltage as a function of the position of the leading coil 37 along the longitudinal axis "X" of the heat exchange tube 9. This vertical component E(v) of voltage is indicative of the net current differential between the coils 37 and 39 as they are moved along the axis of the tube 9. When the leading coil 37 is the position illustrated in FIG. 3A, it is clear that the oscilloscope 49 of the eddy current circuitry 45 is just beginning to trace the top half of the lissajous figurine (which is a curve shaped like a "FIG. 8"), as illustrated in FIG. 3B. In FIG. 3C, it is further evident that the vertical voltage component E(v) of this curve is beginning to trace the foot of one-half of a substantially sinusoidal wave. Before the advent of the invention, it was generally assumed that that the initial pickup in the curves illustrated in FIGS. 3B and 3C indicated that the mid-plane of the leading coil of the eddy current probe 25 was parallel to the edge of the plate structure sought to be detected. However, the invention has shown this interpretation to be in error, as will be evident from the discussion which follows.

Figure 5C:
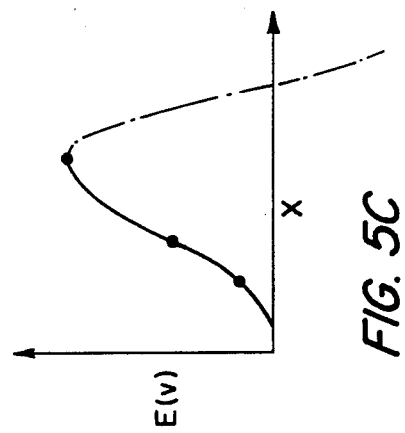
FIGS. 5B and 5C illustrate the reduced rate of change and the maximum in the differential current between the leading and the trailing coils when the eddy current probe is at the position illustrated in FIG. 5A, both with reference to the oscilloscope presentation and the vertical component of the composite waveform, respectively.
Figure 6C:
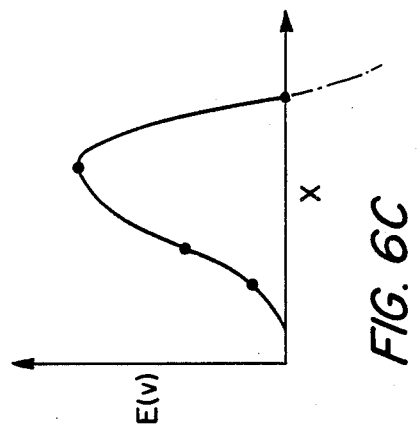
FIGS. 6B and 6C illustrate the null-point in the differential current which occurs when the probe is positioned as illustrated in FIGS. 6A, both with reference to the oscilloscope presentation and the vertical voltage component of the composite waveform, respectively.
Figure 5B:
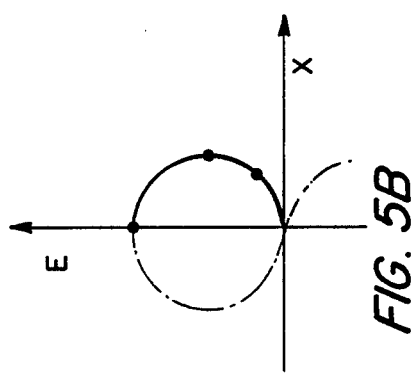
Figure 6B:
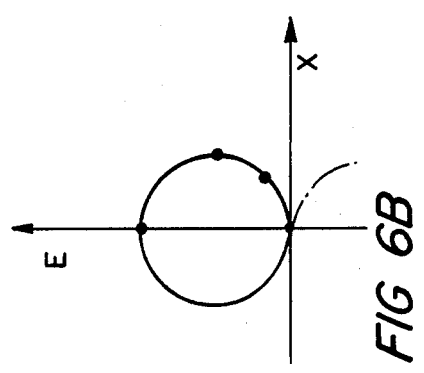
Figure 5A:
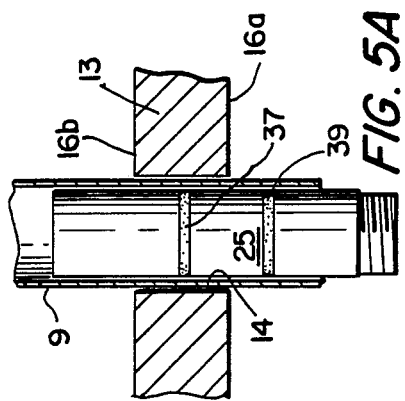
FIG. 5A illustrates the eddy current probe with its leading coil approximately aligned with the center of the support plate, and its trailing coil approaching the bottom edge of this plate.

FIGS. 4A, 4B and 4C are of particular interest with respect to illustrating one of the key concepts behind the invention. When the mid-plane of the coil 37 is parallel with the proximal edge of the plate 13 as illustrated in FIG. 4A, an inflection point occurs in the vertical voltage E(v) curve illustrated in FIG. 4C. This inflection point indicates that the rate of change in the differential impedance (and hence differential current) between the coils 37 and 39 has attained a local maximum. It should be noted that this inflection point in the vertical component voltage E(v) is seen only if the "FIG. 8"-shaped lissajous figurine on the oscilloscope is oriented vertically, as in FIG. 4B. If the thickness of the plate 13 is known, the process of the invention could end at this point, since the upper edge of the plate formed by the upper surface 16b and the wall of the bore 14 may be inferentially determined by adding the plate thickness to the axial distance "X" corresponding to the inflection point in the vertical voltage E(v) curve. However, in the preferred embodiment of the invention, the monitoring of both the vertical voltage E(v) component and the waveform on the oscilloscope of the differential current between the two coils 37 and 39 does not end until the leading coil 37 of the probe 25 is pushed completely through the section of the tube 9 circumscribed by the bore 14 of the baffle plate 13. When the leading coil 37 advances to the position in the tube 9 illustrated in FIG. 5A, the lissajous figurine and the curve of its vertical voltage E(v) component assume the shapes illustrated in FIGS. 5B and 5C, respectively. Vertical voltage E(v) curve indicates that, when leading coil 37 and trailing coil 39 are so positioned, the differential current between them is at a maximum. Applicants believe that this is due to the fact that the magnetic field lines generated by the alternating current in the leading coil 37 are having a maximum amount of electromagnetic coupling of the surrounding plate 13, while the interaction between the magnetic field lines generated by the alternating current in the trailing coil 39 are only negligibly interacting with plate 13.

Figure 6A:
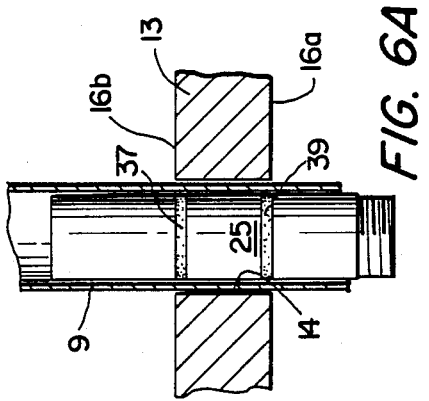
FIG. 6A illustrates the eddy current probe of FIG. 2A with its leading and trailing coils aligned with the top and bottom edges, respectively of the support plate.

When leading and trailing coils 37 and 39 are symmetrically disposed across the edges of the baffle plate 13 in the position illustrated in FIG. 6A, the amount of electromagnetic coupling between the coils 37, 39 and the plate 13 is essentially identical. Therefore, no differential current flows across the electrical bridge in the eddy current circuitry 45. Both the lissajous figurine and the curve of its vertical voltage E(v) component indicate this lack of different current flow by intersecting the zero points on their respective vertical axes in FIGS. 6B and 6C as shown. The location in the graphs where these intersections occur are known as null points. If the mid-planes of the coils are spaced apart along the longitudinal axis of the probe body 27 the same distance as the thickness of the plate 13, these null points in the graphs of FIGS. 6B and 6C will indicate that the mid-plane of the leading coil 37 is parallel to the top edge of the plate 13.

If the probe 25 is finally pushed completely through the section of the tube 9 surrounded by the bore 14 of the plate 13, the shapes of both the lissajous figurine and the vertical voltage E(v) component of this curve will replicate themselves in all material respects, the only difference being the polarity of the curves. Therefore, in order to avoid prolixity, no specific description of the shapes of these curves will be given. It is only necessary to note that when the trailing coil 39 becomes aligned with the top edge of the baffle plate, an inflection point will occur in the vertical voltage E(v) curve. This inflection point provides useful information in that it provides an accurate indication of the location of the top edge of the plate 13 which is independent of whether or not the coils 37 and 39 are spaced apart the same distance as the thickness of the plate.

An alternative embodiment of the process of the invention may be used to determine whether or not a tube expansion has been correctly placed within the edges of a baffle plate or support plate. In this embodiment of the invention, the probe 25 including the leading and trailing coils 37 and 39 is slid through the heat exchange tube 9 in precisely the same fashion as heretofore described, the single material difference being that two alternating currents of substantially different frequencies are conducted through at least one of the coils. Specifically, while a relatively low frequency alternating current (for example, between 5 and 15 kHz) of the same voltage is conducted simultaneously through both the leading and trailing coils 37 and 39, an additional, relatively high frequency alternating current is conducted through at least one of the coils, which will be chosen, throughout the balance of this description, to be the leading coil 37. In the preferred embodiment, this additional alternating current has a frequency of between 400 and 800 kHz. The frequency of this second alternating current conducted through the leading coil 37 is preferably substantially higher than the current used to detect the edges of the plate 13 in order that the magnetic lines of flux will be foreshortened to the point where they interact almost exclusively with the expanded walls of the tube 9 by virtue of the "skin" effect, and do not penetrate through these walls to significantly interact with the metal in the baffle plate 13.

FIGS. 7A, 7B and 7C illustrate how this variation of the invention may be used to determine whether or not a tube expansion is correctly aligned between the top and bottom edges of a bore 14 in the plate 13. FIG. 7A illustrates a correctly aligned radial expansion of such a tube 9. Note that the central portion of the expansion (i.e., that part of the expansion which does not include the tapered, transitional regions of the tube 9) lies completely between the top and bottom edges of the bore 14 in the plate 13. FIGS. 7B and 7C illustrate the vertical voltage E(v) component of the lissajous figurine of the differential current between the two coils along the longitudinal axis "X" of the tube, as well as the amplitude of the impedance "z" to the high frequency current flowing through leading coil 37, respectively. The segment X1, X2 indicates the thickness of the plate 13, and its position along the longitudinal axis of the tube 9. Similarly, the segment X3, X4 of the impedance "z" graph illustrated in FIG. 7C illustrates both the length and axial position of the central portion of the radial expansion in the tube 9. When the tube 9 is correctly expanded between the top and bottom edges of the baffle plate 13, the segment X3, X4 will be included within the segment X1, X2 along the longitudinal axis "X" of the tube 9. However, a reading which indicates that the segment X3, X4 falls outside either of the limits of the segment X1, X2 along the longitudinal axis of the tube 9 would indicate that the central portion of the radial expansion in the tube 9 did not occur entirely against the walls of the bore 14 of the plate 13, and that a part of this expansion occurred over either the top or bottom edge of the plate 13. When any part of the peak of the bell-shaped Z curve falls outside either of the limits of the segment X1, X2, a bulge condition is indicated. As previously mentioned, such bulges are frequently accompanied by an excessive amount of crystal-dislocating strain in at least a portion of the tube 9 in the vicinity of the plate 13, which renders the tube 9 more prone to corrosion degradation from the salts and sludges in the water flowing through the secondary side of the nuclear steam generator. Accordingly, the positive detection of such a bulge condition provides the opportunity for a preventative maintenance operation, such as sleeving or plugging, in order to prevent any problems in the walls of the tube resulting from corrosion degradation of the metal in this area.

It should be noted that, while the second embodiment of the process of the invention has been described in terms of the use of a two-coiled eddy current probe, a single coil eddy current probe could also be used. However, instead of the substantially sinusoidal waveform generated by the two-coil probe, the one-coil probe would provide two substantially bell-shaped curves. Specifically, a plot of the change of the impedance z of the lower frequency current over the longitudinal axis x of the tube would generate a bell-shaped curve whose inflection points on either side would define the segment $\times 1$, $\times 2$ which would contain the peak of the bell-shaped curve provided by the impedance plot of the higher frequency current if the expansion has been properly positioned.

What is claimed is:

1. A process for using an eddy current probe having a coil with an alternating current flowing therethrough to locate the edge of a metallic structure having an edge, comprising the steps of:
   (a) linearly moving said probe through the vicinity of said structure so that it passes by the edge of the structure sufficieintly close to electromagnetically interact therewith;
   (b) monitoring the rate of change of impedance of said coil as a function of the position of the coil with respect to the edge of said structure, and
   (c) locating the edge of said structure by noting the position of the coil along its linear path of motion wherein the rate of change of impedance attains a first maximum.

2. The process defined in claim 1, wherein the structure is substantially orthogonal to the linear path of motion, and said coil is cylindrical, and the axis of rotation of said cylindrical coil is oriented parallel to a surface of said edge.

3. The process defined in claim 1, wherein said structure is a metallic plate.

4. The process defined in claim 1, wherein the edge of said structure is adjacent a conduit, and said probe is moved through said conduit along the longitudinal axis thereof in the vicinity of the structure.

5. The process defined in claim 1, wherein said coil is a bobbin-type coil having a radius which is greater than its length.

6. The process defined in claim 4, wherein said conduit is a tube, and said structure is a metallic plate of substantially uniform thickness having a bore through which said conduit extends.

7. The process defined in claim 1, wherein said alternating current flowing through said coil has a frequency of between about 5 and 15 kHz.

8. The process defined in claim 6, wherein said plate is formed from an alloy including iron.

9. A process of using an eddy current probe having a cylindrical coil with an alternating current flowing therethrough to locate the edges of a metallic structure which is adjacent a conduit, comprising the steps of;
   (a) linearly moving said probe through said conduit through the vicinity of said structure with the axis of rotation of the coil oriented parallel to the longitudinal axis of the conduit wherein said coil passes sufficiently close to the structure so that the coil electromagnetically interacts with the structure;
   (b) monitoring the rate of change of current flow through said coil resulting from eddy currents induced in said structure as a function of the position of the coil along the longitudinal axis of said conduit, and
   (c) locating the proximal and distal edges of said structure by noting the position of said coil along the longitudinal axis of said conduit wherein the coil impedance attains its first and second maximum, respectively.

10. A process of using a differential current eddy current probe of the type including substantially identical leading and trailing cylindrical coils having coincident axes of rotation to locate the proximal edge of a metallic structure having an edge which is adjacent a conduit, comprising the steps of:
    (a) linearly moving said leading and said trailing coils through said conduit through the vicinity of said structure with the axes of rotation of the coils oriented substantially parallel to the longitudinal axis of the conduit, said coils passing sufficiently close to the structure to electromagnetically interact therewith;
    (b) monitoring the rate of change of the differential current flow between the two coils as a function of the longitudinal position of said leading coil in said conduit, and
    (c) noting the position of said leading coil along the longitudinal axis of said conduit wherein the rate of change of said differential current flow attains its first maximum, and
    (d) noting the position of the leading coil when there is substantially no differential current flow between the two coils.

11. The process defined in claim 10, wherein said conduit is a tube.

12. The process defined in claim 10, wherein said structure is metallic.

13. The process defined in claim 10, wherein said structure is a metallic plate which substantially circumscribes said conduit.

14. The process defined in claim 10, wherein said conduit is a tube, and said structure is a metallic plate having a proximal surface which is substantially orthogonally disposed to the longitudinal axis of said tube.

15. The process defined in claim 10, wherein both said leading and said trailing coils are bobbin-type coils, each having the same number of windings.

16. The process defined in claim 10, wherein said conduit is a tube, and said structure is a metallic plate of substantially uniform thickness having a bore through which said conduit extends.

17. The process defined in claim 10, wherein said plate is formed from an alloy including iron.

18. A process of using an eddy current probe having a bobbin-type coil with an alternating current flowing therethrough to locate the proximal edge of an electrically conductive plate which at least partially circumscribes a conduit, comprising the steps of:
    (a) moving said probe through said conduit through the vicinity of said plate with the axis of rotation of the coil oriented parallel to the longitudinal axis of the conduit;
    (b) monitoring the rate of change of impedance of said coil as a function of the position of the coil along the longitudinal axis of said conduit, and
    (c) noting the position of the coil along the longitudinal axis of said conduit wherein the rate of change of impedance attains its first maximum.

19. The process defined in claim 18, further including the step of noting the position of the coil along the longitudinal axis of said conduit wherein the rate of change of coil impedance attains its second maximum in order to locate the distal edge of said plate.

20. A process for determining whether or not the longitudinal limits of an expanded portion of an elongated conduit is contained within the longitudinal limits of a metallic structure that at least partially circumscribes said conduit by means of an eddy current probe having a cylindrical coil, comprising the steps of:
  (a) passing alternating currents of first and second frequencies through said coil, wherein said first frequency is higher than said second frequency;
  (b) moving said coil through said conduit through the vicinity of said expanded portion and said circumscribing structure with the axis of rotation of the coil oriented substantially parallel to the longitudinal axis of the conduit;
  (c) monitoring the rate of change of impedance to said current flow of said first frequency while simultaneously monitoring the rate of change of impedance to said current flow of said second frequency, respectively;
  (d) noting the limits and position of the central portion of said expanded portion of said conduit by noting the position of the coil along the longitudinal axis of said conduit when the coil impedance to said first frequency current first begins to increase over a first impedance, and then returns to said first impedance;
  (e) noting the limits and position of said structure across the longitudinal axis of said conduit by noting the position of the coil when the rate of change of said impedance to said second current flow attains a first and a second maximum, and
  (f) comparing the limits and position of the central portion of said expanded portion with the limits and position of said structure.

21. The process defined in claim 20, wherein said frequency of said first alternating current is at least twice as great as said frequency of said second alternating current.

22. The process defined in claim 20, wherein said frequency of said first alternating current is between about 400 and 800 kHz.

23. The process defined in claim 20, wherein said frequency of said second alternating current is between about 5 and 15 kHz.

24. The process defined in claim 20, wherein said frequency of said first alternating current is between 400 and 800 kHz, and said frequency of said second alternating current is between 5 and 15 kHz.

25. The process defined in claim 20, wherein said structure is an electrically conductive plate, and said conduit is a metallic tube which extends through a bore in said plate.

26. The process defined in claim 24, wherein said structure is a plate formed from an iron alloy, and said conduit is a tube formed from an alloy of nickel, chromium and iron which extends through a bore in said plate.

27. The process defined in claim 20, wherein said coil is a bobbin-type coil having a length substantially less than its radius.

28. A process of utilizing an eddy current detector having a leading and a trailing cylindrical coil for determining, in a tube expansion for reducing the clearance between the tube and a structure surrounding a length of said tube, whether or not said tube expansion extends beyond the length of said structure across said tube, comprising the steps of:
  (a) passing alternating currents of first and second frequencies through said leading coil, wherein said first frequency is substantially higher than said second frequency, while passing an alternating current of said second frequency through said trailing coil;
  (b) moving said leading and said trailing coils through said tube through the vicinity both of said tube expansion and said surrounding structure with the axes of rotation of the coils oriented substantially parallel to the longitudinal axis of the tube;
  (c) monitoring the rate of change of said current flow of said first frequency through said leading coil while simultaneously monitoring the rate of change of the differential current flow between said current flows of said second frequency flowing through said leading and said trailing coils, respectively;
  (d) noting the amount of current flow of said current of said first frequency when said leading coil is in said tube but not in the vicinity of said tube expansion;
  (e) ascertaining the limits and position of said tube expansion by noting the position of the leading coil along the longitudinal axis of said tube
    (i) when there is a substantial increase in the current flow of said first frequency through said leading coil over said noted flow, and
    (ii) when the current flow through said coil of said first frequency resumes said noted flow;
  (f) noting the limits and position of said structure across the longitudinal axis of said tube by noting the position of the leading coil when the rate of change of said differential current flow attains a first and then a second maximum, and
  (g) comparing the limits and position of said tube expansion with the limits and position of said surrounding structure.

* * * * *